United States Patent
Case

(10) Patent No.: US 10,316,288 B2
(45) Date of Patent: Jun. 11, 2019

(54) NEURAL REGENERATING CELLS WITH ALTERATIONS IN DNA METHYLATION

(75) Inventor: Casey Case, San Mateo, CA (US)

(73) Assignee: SanBio, Inc., Mountain View, CA (US)

( * ) Notice: Subject to any disclaimer, the term of this patent is extended or adjusted under 35 U.S.C. 154(b) by 2380 days.

(21) Appl. No.: 12/736,665

(22) PCT Filed: Apr. 30, 2009

(86) PCT No.: PCT/US2009/002664
§ 371 (c)(1),
(2), (4) Date: Feb. 9, 2011

(87) PCT Pub. No.: WO2009/134409
PCT Pub. Date: Nov. 5, 2009

(65) Prior Publication Data
US 2011/0136114 A1    Jun. 9, 2011

(51) Int. Cl.
| | |
|---|---|
| *C12N 5/00* | (2006.01) |
| *C12N 5/079* | (2010.01) |
| *C12Q 1/6881* | (2018.01) |
| *C12Q 1/6883* | (2018.01) |
| *C12N 5/0775* | (2010.01) |

(52) U.S. Cl.
CPC ......... *C12N 5/0618* (2013.01); *C12N 5/0663* (2013.01); *C12Q 1/6881* (2013.01); *C12Q 1/6883* (2013.01); *C12N 2501/42* (2013.01); *C12N 2506/1353* (2013.01); *C12N 2510/00* (2013.01); *C12Q 2600/156* (2013.01)

(58) Field of Classification Search
CPC ............... C12N 5/0618; C12N 5/0663; C12N 2501/42; C12N 2506/135; C12N 2510/00; C12Q 1/6881; C12Q 1/6883; C12Q 2600/156
See application file for complete search history.

(56) References Cited

U.S. PATENT DOCUMENTS

| | | | |
|---|---|---|---|
| 5,486,359 A | 1/1996 | Caplan et al. | |
| 5,591,625 A | 1/1997 | Gerson et al. | |
| 5,789,538 A | 8/1998 | Rebar et al. | |
| 5,843,780 A | 12/1998 | Thomson | |
| 5,925,523 A | 7/1999 | Dove et al. | |
| 6,007,988 A | 12/1999 | Choo et al. | |
| 6,013,453 A | 1/2000 | Choo et al. | |
| 6,140,081 A | 10/2000 | Barbas | |
| 6,140,466 A | 10/2000 | Barbas et al. | |
| 6,200,759 B1 | 3/2001 | Dove et al. | |
| 6,200,806 B1 | 3/2001 | Thomson | |
| 6,242,568 B1 | 6/2001 | Barbas et al. | |
| 6,280,718 B1 | 8/2001 | Kaufman et al. | |
| 6,410,248 B1 | 6/2002 | Greisman et al. | |
| 6,453,242 B1 | 9/2002 | Eisenberg et al. | |
| 6,479,626 B1 | 11/2002 | Kim et al. | |
| 6,534,261 B1 | 3/2003 | Cox et al. | |
| 6,602,711 B1 | 8/2003 | Thomson et al. | |
| 6,610,512 B1 | 8/2003 | Barbas | |
| 6,613,568 B2 | 9/2003 | Kaufman et al. | |
| 6,733,970 B2 | 5/2004 | Choo et al. | |
| 6,746,838 B1 | 6/2004 | Choo et al. | |
| 6,790,941 B2 | 9/2004 | Barbas et al. | |
| 6,794,136 B1 | 9/2004 | Eisenberg et al. | |
| 6,866,997 B1 | 3/2005 | Choo et al. | |
| 6,887,706 B2 | 5/2005 | Zhang et al. | |
| 6,989,271 B2 | 1/2006 | Dezawa et al. | |
| 7,005,252 B1 | 2/2006 | Thomson | |
| 7,029,847 B2 | 4/2006 | Joung et al. | |
| 7,029,913 B2 | 4/2006 | Thomson | |
| 7,067,617 B2 | 6/2006 | Barbas | |
| 7,297,491 B2 | 11/2007 | Joung et al. | |
| 7,682,825 B2 | 3/2010 | Dezawa et al. | |
| 8,092,792 B2 | 1/2012 | Dezawa et al. | |
| 8,133,725 B2 | 3/2012 | Dezawa et al. | |
| 8,361,456 B2 | 1/2013 | Dezawa et al. | |
| 8,945,919 B2 | 2/2015 | Mori et al. | |
| 8,969,078 B2 | 3/2015 | Dezawa et al. | |
| 2002/0165356 A1 | 11/2002 | Barbas | |
| 2002/0188103 A1 | 12/2002 | Bestor | |
| 2003/0003090 A1 | 1/2003 | Prockop et al. | |

(Continued)

FOREIGN PATENT DOCUMENTS

| | | |
|---|---|---|
| EP | 1479767 | 11/2004 |
| GB | 2338237 | 12/1999 |

(Continued)

OTHER PUBLICATIONS

Long et al. "Neural Cell Differentiation In Vitro from Adult Human Bone Marrow Mesenchymal Stem Cells." Stem Cells and Development (2005); 14(1):pp. 65-69.*

Huang and Fan. "DNA methylation in cell differentiation and reprogramming: an emerging systematic view." Regen Med. Jul. 2010;5(4):531-44.*

Kohayam, et al., "Brain From Bone: Efficient "Meta-Differentiation" of Marrow Stroma-Derived Mature Osteoblasts to Neurons With Noggin or a Demethylating Agent," *Differentiation* 68(4-5):235-244 (2001).

Leong, et al., "JAGGED1-Mediated Notch Activation Induces Epithelial-To-Mesenchymal Transition Through Slug-Induced Repression of E-Cadherin," *JEM* 204(12):2935-2948 (2007).

Rapko, et al., "DNA Methylation Analysis as a Novel Tool for Quality Control in Regenerative Medicine," *Tissue Engineering* 13(9):2271-2280 (2007).

(Continued)

*Primary Examiner* — Titilayo Moloye
(74) *Attorney, Agent, or Firm* — Levine Bagade Han LLP

(57) ABSTRACT

Disclosed herein are cells, that are descendents of marrow adherent stem cells (MASCs), capable of rescuing and/or reversing various neural disorders after transplantation into sites of central nervous system (CNS) or peripheral nervous system (PNS) injury. The cells contain alterations in the methylation state of certain genes, compared to their methylation state in MASCs. Methods of making cells capable of rescuing and/or reversing various neural disorders after transplantation into sites of CNS or PNS injury, by alteration of the methylation status of certain genes, are also provided.

6 Claims, No Drawings

Specification includes a Sequence Listing.

(56) References Cited

U.S. PATENT DOCUMENTS

| | | |
|---|---|---|
| 2003/0108880 A1 | 6/2003 | Rebar |
| 2003/0119023 A1 | 6/2003 | Choo et al. |
| 2004/0091878 A1 | 5/2004 | Sera |
| 2004/0197892 A1 | 10/2004 | Moore et al. |
| 2006/0166362 A1 | 7/2006 | Dezawa et al. |
| 2006/0216276 A1 | 9/2006 | Dezawa et al. |
| 2007/0009948 A1 | 1/2007 | Choo et al. |
| 2007/0009962 A1 | 1/2007 | Choo et al. |
| 2007/0105792 A1 | 5/2007 | Di Martino |
| 2007/0154989 A1 | 7/2007 | Barbas et al. |
| 2007/0213269 A1 | 9/2007 | Barbas et al. |
| 2010/0034790 A1 | 2/2010 | Dezawa et al. |
| 2010/0144034 A1 | 6/2010 | Dezawa et al. |
| 2010/0266554 A1 | 10/2010 | Mori et al. |
| 2010/0310523 A1 | 12/2010 | Dezawa et al. |
| 2010/0310529 A1 | 12/2010 | Aizman |
| 2011/0229442 A1 | 9/2011 | Dezawa |
| 2011/0306137 A1 | 12/2011 | Aizman |
| 2013/0071924 A1 | 3/2013 | Dezawa et al. |
| 2014/0363408 A1 | 12/2014 | Aizman et al. |

FOREIGN PATENT DOCUMENTS

| | | |
|---|---|---|
| JP | 2003-144155 | 5/2003 |
| WO | WO 1997/11972 | 4/1997 |
| WO | WO 1997/011972 | 4/1997 |
| WO | WO 1998/037186 | 8/1998 |
| WO | WO 1998/053059 | 11/1998 |
| WO | WO 2001/053480 | 7/2001 |
| WO | WO 2001/060970 | 8/2001 |
| WO | WO 2002/077272 | 3/2002 |
| WO | WO 2002/057293 | 7/2002 |
| WO | WO 2003/016496 | 2/2003 |
| WO | WO 2006/094836 | 9/2006 |
| WO | WO 2008/102460 | 8/2008 |
| WO | WO 2009/023251 | 2/2009 |

OTHER PUBLICATIONS

Yamasaki, et al., "Neuron-Specific Relaxation of IGF2R Imprinting is Associated With Neuron-Specific Histone Modifications and Lack of Its Antisense Transcript Air," *Hum. Mol. Genet.* 14(17):2511-20 (2005).
Artavanis-Tsakonas, et al., "Notch Signaling," *Science* 268:225-232 (1995).
Beerli, et al., "Engineering Polydactyl Zinc-finger Transcription Factors," *Nature Biotechnol.* 20:135-141 (2002).
Bhattacharya, et al., "A Mammalian Protein With Specific Demethylase Activity for mCpG DNA," *Nature (London)* 397:579-583 (1999).
Campagnoli, et al., "Identification of Mesenchymal Stem/Progenitor Cells in Human First-Trimester Fetal Blood, Liver and Bone Marrow," *Blood* 98:2396-2402 (2001).
Cervoni, et al., "DNA Demethylase is a Processive Enzyme," *J. Bio. Chem.* 274:8363-8366 (1999).

Choo, et al., "Advances in Zinc Finger Engineering," *Curr. Opin. Struct. Biol.* 10:411-416 (2000).
Dezawa, et al., "Sciatic Nerve Regeneration in Rats Induced by Transplantation of in vitro Differentiated Bone-marrow Stromal Cells," *Eur. J. Neurosci.* 14:1771-1776 (2001).
Dezawa, et al., "Specific Induction of Neuronal Cells from Bone Marrow Stromal Cells and Application for Autologous Transplantation," *Journal of Clinical Investigation* 113: 1701-1710 (2004).
Ehebauer, et al., "Notch Signaling Pathway," *Sci. STKE* 2006 (364), cm7 [DOI: 10.1126/stke.3642006cm7].
Erices, et al., "Mesenchymal Progenitor Cells in Human Umbilical Cord Blood", *Br. J. Haematol* 109:235-242 (2000).
Hou, et al., "Induction of Umbilical Cord Blood Mesenchymal Stem Cells Into Neuron-Like Cells in Vitro," *Int. J. Hematol.* 78:256-261 (2003).
Isalan, et al., "A Rapid, Generally Applicable Method to Engineer Zinc Fingers Illustrated by Targeting the HIV-1 Promoter," *Nature Biotechnol.* 19:656-660 (2001).
Jiang, et al., "Pluripotency of Mesenchymal Stem Cells Derived from Adult Marrow," *Nature* 418:41-49 (2002).
Miller, et al., "Repetitive Zinc-binding Domains in the Protein Transcription Factor IIIA from *Xenopus* Oocytes," *EMBO J* 4:1609-1614 (1985).
Moore, et al., "Design of Polyzinc Finger Peptides with Structured Linkers," *Proc. Natl. Acad. Sci. USA* 98:1432-1436 (2001a).
Moore, et al., "Improved DNA Binding Specificity from Polyzinc Finger Peptides by Using Strings of Two-finger Units," *Proc. Natl. Acad. Sci. USA* 98:1437-1441 (2001b).
Mumm and Kopan, "Notch Signaling: From the Outside In," *Develop. Biol.* 228:151-165 (2000).
Pabo, et al., "Design and Selection of Novel $Cys_2His_2$ Zinc Finger Proteins" *Ann. Rev. Biochem.* 70:313-340 (2001).
Pittenger, et al., "Multilineage Potential of Adult Human Mesenchymal Stem Cells," *Science* 284:143-147 (1999).
Prockop, et al., "Marrow Stromal Cells as Stem Cells for Nonhematopoietic Tissues," *Science* 276:71-74 (1997).
Rhodes, et al., "Zinc Fingers—They play a key part in regulating the activity of genes in many species, from yeast to humans. Fewer than 10 years ago no one knew they existed," *Scientific American* February:56-65 (1993).
Segal, et al., "Custom DNA-binding Proteins Come of Age: Polydactyl Zinc-finger proteins," *Curr. Opin. Biotechnol.* 12:632-637 (2001).
Kageyama, et al., "Roles of HES Genes in Neural Development," *Dev Growth Differ* 50(1):S97-103 (2008).
Snowden, et al., "Gene-Specific Targeting of H3K9 Methylation is Sufficient for Initiating Repression In Vivo," *Current Biology* 12:2159-2166 (2002).
Watanbe, et al., "Transition of Mouse De Novo Methyltransferases Expression From DNMT3B to DNMT3A During Neural Progenitor Cell Development," *Neuroscience* 142(3):727-37 (2006).
Ali et al. (2008) Cell Transplantation 17:458.
Dezawa et al. (2005) Expert Opinion Biological Therapy 5:427-435.
Dezawa (2003) Acta Anatomica Nipponica 78(suppl):97 (Abstract S04-6).

\* cited by examiner

NEURAL REGENERATING CELLS WITH ALTERATIONS IN DNA METHYLATION

CROSS-REFERENCE TO RELATED APPLICATIONS

This application is a 35 U.S.C. § 371 filing of PCT/US2009/002664, filed Apr. 30, 2009, PCT/US2009/002664 claims the benefit of U.S. provisional application No. 61/125,978 (filed Apr. 30, 2008), the disclosure of which is incorporated by reference in its entireties for all purposes.

STATEMENT REGARDING FEDERAL SUPPORT

Not applicable.

FIELD

The present disclosure is in the fields of cellular therapy for neural disorders and epigenetic regulation of gene expression and differentiation.

BACKGROUND

Cellular differentiation is controlled, in part, by regulation of gene expression. Regulation of transcription; i.e., use of DNA as a template for the synthesis of a mRNA molecule; is one of the mechanisms by which gene expression is regulated. Transcriptional regulation of gene expression can result, for example, from alteration of chromatin structure and/or binding of transcriptional regulatory proteins to specific DNA sequences in or near the gene.

Another means by which transcriptional control of gene expression is effected is by chemical alteration of DNA. The most widely-studied aspect of this form of regulation is DNA methylation. In eukaryotic genomes, the primary form of DNA methylation is the conversion of cytosine to 5-methyl-cytosine, through the action of one of a number of cellular methyltransferases. In most cases, methylated C residues are located directly upstream of a G residue. In general, methylation of C residues in or near a gene is correlated with reduced expression of the gene. In most cases, CpG methylation is not itself the proximate cause of transcriptional repression of a gene, but appears to be a mechanism to perpetuate transcriptional repression initially mediated by gene regulatory proteins.

The frequency of CG dinucleotide sequences in the upstream regions of certain non-cell-type-specific vertebrate genes (i.e., housekeeping genes) is much higher than would be expected based on the GC content of the genome; such regions are known as CpG Islands. CpG Islands are sites at which the methylation state of the C residues can affect transcription of the associated gene. Conversely, the methylation state of C residues in a CpG island or other region associated with a particular gene can be used as a potential indicator of the transcriptional state of that gene and/or as a diagnostic marker to characterize a particular cell type. See, for example, WO 2006/094836.

SUMMARY

Disclosed herein are cells that are capable of stimulating neural recovery and/or neural regeneration after transplantation to sites of nervous system injury or disease. In certain embodiments, the cells are descended from marrow adherent stem cells (MASCs), but have undergone alterations in the methylation status of certain genes after treatment and culture in vitro. Thus, the inventor has discovered that alteration of the methylation state of one or more genes can convert a progenitor cell into a descendent cell having neural regenerative properties not possessed by the progenitor cell.

As a result of this discovery, the present disclosure encompasses, inter alia, the following embodiments:

1. A method for altering the methylation state of a gene in a cell, the method comprising:
   (a) transfecting the cell with a polynucleotide comprising sequences encoding a Notch intracellular domain; and
   (b) culturing the transfected cell such that the methylation state of a gene in the cell or one or more descendents of the cell is altered as compared to the gene in an untransfected cell, thereby altering the methylation state of the gene.

2. The method of embodiment 1, wherein the gene is the PITX2 gene.

3. The method of embodiment 1, wherein the gene is the DNMT3b gene.

4. The method of embodiment 1, wherein the gene is the IGF2R gene.

5. The method of embodiment 1, wherein the gene is the SDF4 gene.

6. The method of embodiment 1, wherein the gene is the ROPN1L gene.

7. The method of embodiment 1, wherein the gene is the TMEM179 gene.

8. The method of any of embodiments 1-5, wherein methylation of the gene is increased in the descendent cell.

9. The method of any of embodiments 1 6 or 7, wherein methylation of the gene is decreased in the descendent cell.

10. The method of embodiment 9, wherein the sequence C-A-T-$C^{me}$-G-C-C-C is converted to C-A-T-C-G-C-C-C.

11. The method of any of embodiments 1-10, wherein the cell is a marrow adherent stromal cell (MASC).

12. A method for making a descendent cell in which the methylation state of a gene is altered, the method comprising:
   (a) transfecting a progenitor cell with a polynucleotide comprising sequences encoding a Notch intracellular domain;
   (b) culturing the transfected cell; and
   (c) obtaining, among the progeny of the transfected cell, one or more descendent cells in which the methylation state of the gene is altered.

13. The method of embodiment 12, wherein the gene is the PITX2 gene.

14. The method of embodiment 12, wherein the gene is the DNMT3b gene.

15. The method of embodiment 12, wherein the gene is the IGF2R gene.

16. The method of embodiment 12, wherein the gene is the SDF4 gene.

17. The method of embodiment 12, wherein the gene is the ROPN1L gene.

18. The method of embodiment 12, wherein the gene is the TMEM179 gene.

19. The method of any of embodiments 12-16, wherein methylation of the gene is increased in the descendent cell compared to the progenitor cell.

20. The method of any of embodiments 12 or 17 or 18, wherein methylation of the gene is decreased in the descendent cell compared to the progenitor cell.

21. The method of embodiment 20, wherein the sequence C-A-T-$C^{me}$-G-C-C-C is converted to C-A-T-C-G-C-C-C.

22. The method of any of embodiments 12-21, wherein the progenitor cell is a marrow adherent stromal cell (MASC).

23. A method for converting a progenitor cell to a neural regenerating cell, the method comprising altering the methylation state of one or more genes in the progenitor cell.

24. The method of embodiment 23, wherein the gene is the PITX2 gene.

25. The method of embodiment 23, wherein the gene is the DNMT3b gene.

26. The method of embodiment 23, wherein the gene is the IGF2R gene.

27. The method of embodiment 23, wherein the gene is the SDF4 gene.

28. The method of embodiment 23, wherein the gene is the ROPN1L gene.

29. The method of embodiment 23, wherein the gene is the TMEM179 gene.

30. The method of any of embodiments 23-27, wherein methylation of the gene is increased in the neural regenerating cell, compared to the progenitor cell.

31. The method of any of embodiments 23, 28 or 29, wherein methylation of the gene is decreased in the neural regenerating cell, compared to the progenitor cell.

32. The method of embodiment 31, wherein the sequence C-A-T-$C^{me}$-G-C-C-C is converted to C-A-T-C-G-C-C-C.

33. The method of any of embodiments 23-32, wherein the progenitor cell is a marrow adherent stromal cell (MASC).

34. The method of embodiment 23, wherein the methylation state of the gene is altered by:
(a) transfecting the progenitor cell with a polynucleotide comprising sequences encoding a Notch intracellular domain;
(b) culturing the transfected cell; and
(c) obtaining, among the progeny of the transfected cell, one or more descendent cells in which the methylation state of the gene is altered;
wherein said descendent cell in which the methylation state of the gene is altered is a neural regenerating cell.

35. The method of embodiment 30, wherein the methylation state of the gene is altered by contacting the progenitor cell with a fusion protein comprising a methylation domain and a DNA-binding domain, or with a nucleic acid encoding a fusion protein comprising a methylation domain and a DNA-binding domain, wherein the DNA binding domain is engineered to bind to one or more sequences in the gene.

36. The method of embodiment 31, wherein the methylation state of the gene is altered by contacting the progenitor cell with a fusion protein comprising a demethylation domain and a DNA-binding domain, or with a nucleic acid encoding a fusion protein comprising a demethylation domain and a DNA-binding domain, wherein the DNA binding domain is engineered to bind to one or more sequences in the gene.

37. A cell that is descended from a progenitor cell through culture in vitro, wherein:
(a) the cell supports the growth and/or regeneration of neural tissue;
(b) the methylation state of one or more genes in the cell is altered compared to the progenitor cell; and
(c) during the culture in vitro, neither the progenitor cell nor any of its descendents were transfected with a polynucleotide comprising sequences encoding the Notch intracellular domain (NICD).

38. The cell of embodiment 37, wherein the gene is the PITX2 gene.

39. The cell of embodiment 37, wherein the gene is the DNMT3b gene.

40. The cell of embodiment 37, wherein the gene is the IGF2R gene.

41. The cell of embodiment 37, wherein the gene is the SDF4 gene.

42. The cell of embodiment 37, wherein the gene is the ROPN1L gene.

43. The cell of embodiment 37, wherein the gene is the TMEM179 gene.

44. The cell of any of embodiments 37-41, wherein methylation of the gene is increased in the neural regenerating cell, compared to the progenitor cell.

45. The cell of any of embodiments 37, 42 or 43, wherein methylation of the gene is decreased in the neural regenerating cell compared to the progenitor cell.

46. The cell of embodiment 45, wherein the sequence C-A-T-$C^{me}$-G-C-C-C is converted to C-A-T-C-G-C-C-C.

47. The cell of any of embodiments 37-46, wherein the progenitor cell is a marrow adherent stromal cell (MASC).

48. The cell of embodiment 37, wherein the methylation state of the gene is altered by contacting the progenitor cell with a fusion protein comprising a methylation domain and a DNA-binding domain, or with a nucleic acid encoding a fusion protein comprising a methylation domain and a DNA-binding domain, wherein the DNA binding domain is engineered to bind to one or more sequences in the gene.

49. The cell of embodiment 37, wherein the methylation state of the gene is altered by contacting the progenitor cell with a fusion protein comprising a demethylation domain and a DNA-binding domain, or with a nucleic acid encoding a fusion protein comprising a demethylation domain and a DNA-binding domain, wherein the DNA binding domain is engineered to bind to one or more sequences in the gene.

50. A method for identifying a neural regenerating cell, the method comprising assaying the methylation state of one or more genes in the cell, wherein a change in the methylation state of the assayed genes is indicative of a neural regenerating cells.

51. The method of embodiment 50, wherein the assay is for increased methylation of the one or more genes.

52. The method of embodiment 50, wherein the assay is for decreased methylation of the one or more genes.

53. The method of embodiment 50, wherein the assay is for increased methylation of one or more first genes and for decreased methylation of one or more second genes.

54. The method of embodiment 50, wherein the one or more genes is/are selected from the group consisting of PITX2, ROPN1L, DNMT3b, IGF2R, TMEM179 and SDF4.

BRIEF DESCRIPTION OF THE DRAWINGS

Not applicable.

DETAILED DESCRIPTION

Methylation State as a Diagnostic

Analysis of changes in the DNA methylation state of specific CpG sequences in or near one or more genes of interest can be used to identify a cell and to distinguish it from other cells with different DNA methylation patterns. For example, if, in a stem or other type of progenitor cell, a particular CpG sequence is methylated on its C residue, and upon further differentiation, the C residue becomes demethylated; the demethylation of that C residue can be used as a marker for that differentiation step. Conversely, methylation of a C residue may serve as a marker for differentiation.

Total, all-or-none changes in methylation state are not required; a change in methylation frequency at a particular CpG sequence can also be diagnostic.

A number of methods, known in the art, can be used to distinguish methylated from unmethylated cytosine residues. These include, but are not limited to, treatment of DNA with bisulfite, and assay of DNA cleavage with methylation-sensitive and methylation-dependent restriction enzymes. Bisulfite ($SO_3^-$) treatment deaminates unmethylated cytosine, converting it to deoxyuridine which, upon replication, templates an adenosine residue in the nascent DNA strand. Thus, bisulfite treatment results in eventual conversion of a C-G base pair into a T-A base pair; and such changes can be detected by standard DNA sequencing methods. Methylated C residues are unaffected by bisulfite treatment; therefore $C^{me}$-G base pairs remain unchanged.

For assay of methylation status using restriction enzymes, enzymes with the sequence CG in their recognition site can be used. For certain recognition sites which contain the sequence CG, an enzyme which recognizes the site will fail to cleave it if the C residue is methylated, but an isoschizomer of that enzyme (i.e., an enzyme that recognizes the same sequence) will cleave the site whether or not the C residue is methylated. For example, both HpaII and MspI recognize the sequence CCGG. MspI cleaves the site regardless of whether the second C residue is methylated. However, HpaII will cleave the site only if the second C residue is unmethylated. Thus, cleavage of a CCGG sequence by both enzymes indicates that the second C residue in the site is unmethylated (i.e., the site has the sequence C-C-G-G); while cleavage by MspI only indicates that the second C residue is methylated (i.e., the site has the sequence C-$C^{me}$-G-G).

In practice, analysis of the methylation state of a particular CpG sequence involves identification of a longer sequence that includes the CpG of interest. This sequence, often denoted an amplicon, is generally chosen so that it includes one or more CpG dinucleotide sequences (at which the methylation state may differ in different cell types) and is suitable for amplification; e.g., by polymerase chain reaction. Such amplicon sequences are generally long enough to be unique in a mammalian-sized genome.

Additional details and other information relating to methylation analysis and exemplary amplicons that can be used for analysis of DNA methylation are found in WO 2006/094836 (Sep. 14, 2006), the disclosure of which is incorporated by reference for the purposes of providing additional details and other information relating to methylation analysis and exemplary amplicons that can be used for analysis of DNA methylation.

Progenitor Cells

Progenitor cells, which can be converted to neural regenerating cells by altering the methylation status of certain genes, can be any type of non-terminally differentiated cell. For example, totipotent stem cells as disclosed for example, in U.S. Pat. Nos. 5,843,780; 6,200,806 and 7,029,913 can be used as progenitor cells. Totipotent stem cells can be cultured (e.g., U.S. Pat. Nos. 6,602,711 and 7,005,252) and differentiated into various types of pluripotent cells (e.g., U.S. Pat. Nos. 6,280,718; 6,613,568 and 6,887,706), which can also be used as progenitor cells in the practice of the disclosed methods.

Another exemplary type of progenitor cells are marrow adherent stromal cells (MASCs), also known as bone marrow stromal cells (BMSCs), marrow adherent stem cells and mesenchymal stem cells. Exemplary disclosures of MASCs are provided in U.S. patent application publication No. 2003/0003090; Prockop (1997) *Science* 276:71-74 and Jiang (2002) *Nature* 418:41-49. Methods for the isolation and purification of MASCs can be found, for example, in U.S. Pat. No. 5,486,359; Pittenger et al. (1999) *Science* 284:143-147 and Dezawa et al. (2001) *Eur. J. Neurosci.* 14:1771-1776. Human MASCs are commercially available (e.g., BioWhittaker, Walkersville, Md.) or can be obtained from donors by, e.g., bone marrow aspiration, followed by selection for adherent bone marrow cells. See, e.g., WO 2005/100552.

MASCs can also be isolated from umbilical cord blood. See, for example, Campagnoli et al. (2001) *Blood* 98:2396-2402; Erices et al. (2000) *Br. J. Haematol.* 109:235-242 and Hou et al. (2003) *Int. J. Hematol.* 78:256-261.

Notch Intracellular Domain

The Notch protein is a transmembrane receptor, found in all metazoans, that influences cell differentiation through intracellular signaling. Contact of the Notch extracellular domain with a Notch ligand (e.g., Delta, Serrate, Jagged) results in two proteolytic cleavages of the Notch protein, the second of which is catalyzed by a γ-secretase and releases the Notch intracellular domain (NICD) into the cytoplasm. In the mouse Notch protein, this cleavage occurs between amino acids gly1743 and val1744. The NICD translocates to the nucleus, where it acts as a transcription factor, recruiting additional transcriptional regulatory proteins (e.g., MAM, histone acetylases) to relieve transcriptional repression of various target genes (e.g., Hes 1).

Additional details and information regarding Notch signaling are found, for example in Artavanis-Tsakonas et al. (1995) *Science* 268:225-232; Mumm and Kopan (2000) *Develop. Biol.* 228:151-165 and Ehebauer et al. (2006) *Sci. STKE* 2006 (364), cm7. [DOI: 10.1126/stke.3642006cm7].

Transfection of progenitor cells (e.g., MASCs) with a nucleic acid encoding the human Notch intracellular domain, followed by enrichment of transfected cells by drug selection and further culture, results in the production of neural regenerating cells with altered DNA methylation in their genomes, See Example 2, infra, for additional details.

Cell Culture and Transfection

Standard methods for cell culture are known in the art. See, for example, R. I. Freshney "Culture of Animal Cells: A Manual of Basic Technique," Fifth Edition, Wiley, N.Y., 2005.

Methods for introduction of exogenous DNA into cells (i.e., transfection) are also well-known in the art. See, for example, Sambrook et al. "Molecular Cloning: A Laboratory Manual," Third Edition, Cold Spring Harbor Laboratory Press, 2001; Ausubel et al., "Current Protocols in Molecular Biology," John Wiley & Sons, New York, 1987 and periodic updates.

Exemplary methods for transfection and culture are provided in Examples 1 and 2, infra.

Methods for Targeted Alteration of DNA Methylation

Because conversion of progenitor cells to neural regenerating cells is accompanied by changes in the methylation state of certain genes; targeted alteration of methylation state can be used to convert a progenitor cell to a neural regenerating cell.

Methods for altering the methylation state at a particular C residue are known in the art. To increase the methylation of a particular sequence, fusion proteins comprising a DNA-binding domain and a methylation domain can be used. See, for example, Bestor U.S. 2002/0188103 (Dec. 12, 2002) and WO 97/11972 (Apr. 3, 1997). Exemplary DNA methyltransferase enzymes, which can serve as a source of methylation domains, are disclosed in the aforementioned references. A DNA methyltransferase is a protein which is capable of methylating a particular DNA sequence, which particular DNA sequence may be CpG. This protein may be a mutated DNA methyltransferase, a wild type DNA methyltransferase, a naturally occurring DNA methyltransferase, a variant of a naturally occurring DNA methyltransferase, a truncated DNA methyltransferase, or a segment of a DNA methyltransferase which is capable of methylating DNA. The DNA methyltransferase may include mammalian DNA methyltransferase, bacterial DNA methyltransferase, M.SssI DNA methyltransferase and other proteins or polypeptides that have the capability of methylating DNA.

Exemplary DNA methyltransferases that can serve as a source of methylation domains for the construction of fusion proteins include, but are not limited to, cytosine DNA methyltransferases, dam methyltransferase, dcm methyltransferase, DNMT1, DNMT2, DNMT3a, DNMT3b, CpG methylases, M.SssI, M.CviPI, HhaI methyltransferase, HpaII methyltransferase, MspI methyltransferase, TaqI methyltransferase, BamHI methyltransferase, EcoRI methyltransferase, HaeIII methyltransferase, AluI methyltransferase, and SssI methyltransferase.

For reducing the degree of methylation of a particular DNA sequence, fusions between a DNA-binding domain and a demethylating domain can be used. Exemplary DNA demethylating domains have been described. See, for example, Bhattacharya et al. (1999) *Nature (London)* 397: 579-583; Cervoni et al. (1999) *J. Biol. Chem.* 274:8363-8366.

Another exemplary method for reducing the degree of methylation of a sequence of interest is to express, in the cell, a fusion between a DNA binding domain (that binds to the sequence of interest) and a 5-methylcytosine DNA-glycosylase. The fusion protein removes the methylated cytosine base from the DNA sugar-phosphate backbone, to be replaced with cytosine by cellular DNA repair enzymes.

Demethylation of a DNA sequence of interest can also be achieved by blocking access of maintenance methylases to that sequence during replication; thereby preventing methylation of the unmethylated strand of newly-replicated hemimethylated DNA. A further round of replication will result in daughter DNA duplexes that are unmethylated at the sequence of interest. Such blockage can be achieved by expression in the cell of a zinc finger DNA-binding domain that is engineered to bind to the sequence of interest (see below).

The activity of a methylation domain or demethylation domain can be targeted to a particular C residue by constructing a fusion protein (or a nucleic acid encoding the fusion protein) comprising a methylation domain and a DNA binding domain, wherein the DNA-binding domain either binds naturally to a sequence at or near the chosen C residue or has been engineered to bind to a sequence at or near the chosen C residue. The DNA-binding domain can be a naturally-occurring DNA-binding domain or a non-naturally-occurring, engineered DNA-binding domain.

In this regard, the zinc finger DNA-binding domain is useful, inasmuch as it is possible to engineer zinc finger proteins to bind to any DNA sequence of choice. A zinc finger binding domain comprises one or more zinc finger structures. Miller et al. (1985) *EMBO J* 4:1609-1614; Rhodes (1993) *Scientific American* February: 56-65; U.S. Pat. No. 6,453,242. Typically, a single zinc finger is about 30 amino acids in length and contains four zinc-coordinating amino acid residues. Structural studies have demonstrated that the canonical ($C_2H_2$) zinc finger motif contains two beta sheets (held in a beta turn which generally contains two zinc-coordinating cysteine residues) and an alpha helix (generally containing two zinc coordinating histidine residues).

Zinc fingers include both canonical $C_2H_2$ zinc fingers (i.e., those in which the zinc ion is coordinated by two cysteine and two histidine residues) and non-canonical zinc fingers such as, for example, $C_3H$ zinc fingers (those in which the zinc ion is coordinated by three cysteine residues and one histidine residue) and $C_4$ zinc fingers (those in which the zinc ion is coordinated by four cysteine residues). Non-canonical zinc fingers can also include those in which an amino acid other than cysteine or histidine is substituted for one of these zinc-coordinating residues. See e.g., WO 02/057293 (Jul. 25, 2002) and US 2003/0108880 (Jun. 12, 2003).

Zinc finger binding domains can be engineered to bind to a sequence of choice. See, for example, Beerli et al. (2002) *Nature Biotechnol.* 20:135-141; Pabo et al. (2001) *Ann. Rev. Biochem.* 70:313-340; Isalan et al. (2001) *Nature Biotechnol.* 19:656-660; Segal et al. (2001) *Curr. Opin. Biotechnol.* 12:632-637; Choo et al. (2000) *Curr. Opin. Struct. Biol.* 10:411-416. Zinc finger binding domain are engineered to have a novel binding specificity, compared to a naturally-occurring zinc finger protein. Engineering methods include, but are not limited to, rational design and various types of empirical selection methods. Rational design includes, for example, using databases comprising triplet (or quadruplet) nucleotide sequences and individual zinc finger amino acid sequences, in which each triplet or quadruplet nucleotide sequence is associated with one or more amino acid sequences of zinc fingers which bind the particular triplet or quadruplet sequence. See, for example, U.S. Pat. Nos. 6,140,081; 6,453,242; 6,534,261; 6,610,512; 6,746,838; 6,866,997; 7,067,617; U.S. Patent Application Publication Nos. 2002/0165356; 2004/0197892; 2007/0154989; 2007/0213269; and International Patent Application Publication Nos. WO 98/53059 and WO 2003/016496.

Exemplary selection methods, including phage display, interaction trap, hybrid selection and two-hybrid systems, are disclosed in U.S. Pat. Nos. 5,789,538; 5,925,523; 6,007,988; 6,013,453; 6,140,466; 6,200,759; 6,242,568; 6,410,248; 6,733,970; 6,790,941; 7,029,847 and 7,297,491; as well as U.S. Patent Application Publication Nos. 2007/0009948 and 2007/0009962; WO 98/37186; WO 01/60970 and GB 2,338,237.

Enhancement of binding specificity for zinc finger binding domains has been described, for example, in U.S. Pat. No. 6,794,136 (Sep. 21, 2004). Additional aspects of zinc finger engineering, with respect to inter-finger linker sequences, are disclosed in U.S. Pat. No. 6,479,626 and U.S. Patent Application Publication No. 2003/0119023. See also Moore et al. (2001a) *Proc. Natl. Acad. Sci. USA* 98:1432-1436; Moore et al. (2001b) *Proc. Natl. Acad. Sci. USA* 98:1437-1441 and WO 01/53480.

All of the references cited in this section, entitled "Methods for targeted alteration of DNA Methylation," are hereby incorporated by reference in their entireties for the purposes of disclosing exemplary methylation domains and demethylation domains (wild-type and mutant), art-recognized methods for the design, selection and engineering of zinc finger DNA-binding domains, and construction of fusion proteins comprising methylation domains and/or zinc finger DNA-binding domains.

EXAMPLES

Example 1: Preparation of Marrow Adherent Stromal Cells (MASCs)

Bone marrow aspirates, obtained from human donors, were divided into 12.5 ml aliquots in 50 ml tubes, and 12.5 ml of growth medium (10% FBS in αMEM, supplemented with penicillin/streptomycin and 2 mM L-glutamine) was added to each tube. The contents of the tubes were mixed by inversion and the tubes were centrifuged at 200×g for 8 minutes. The upper, clear phase was discarded, the volume of the lower phase was adjusted to 25 ml with fresh growth medium, and the tubes were again mixed and centrifuged. The upper layer was again removed. The volume of the lower phase in each tube was again adjusted to 25 ml and the contents of all tubes was pooled in a 250 ml tube. After determination of cell concentration by Trypan Blue exclusion and determination of nucleated cell count, cells were plated in T225 flasks, in 40 ml per flask of growth medium at a density of $100 \times 10^6$ total nucleated cells per flask. The flasks were incubated at 37° C. for 3 days in a $CO_2$ incubator, during which time the MASCs attached to the flask.

After 3 days, unattached cells were removed by rocking the flasks and withdrawing the culture medium. Each flask was washed three times with 40 ml of αMEM supplemented with penicillin/streptomycin; then 40 ml of prewarmed (37° C.) growth medium was added to each flask and the cells were cultured at 37° C. in a $CO_2$ incubator. During this time, the medium was replaced with 40 ml of fresh growth medium every 3-4 days, and cells were monitored for growth of colonies and cell density.

When the cultures achieved 25-30% confluence (usually 10,000-20,000 cells per colony and within 10-14 days), the MASCs (passage M0) were harvested for further passage. MASCs were harvested from up to 10 T-225 flasks at a time. Medium was removed from the flasks and the adherent cells were rinsed with 20 ml of DPBS w/o Ca/Mg (DPBS-/-, HyClone) 2 times. Ten ml of 0.25% Trypsin/EDTA (Invitrogen, Carlsbad, Calif.) was added to each flask and flasks were incubated for approximately 5 min at room temperature. When cells had detached and the colonies had dispersed into single cells, the trypsin was inactivated by addition of 10 ml of growth medium followed by gentle mixing. The cell suspensions were withdrawn from the flasks, and pooled in 250 ml tubes. The tubes were subjected to centrifugation at 200×g for 8 minutes. The supernatants were carefully removed and the wet cell pellets were resuspended in growth medium to an estimated cell concentration of approximately $1 \times 10^6$ cells/ml. Viable cell count was determined and cells were plated in T225 flasks at a concentration of $2 \times 10^6$ cells per flask in growth medium (passage M1). Cells were grown for 3-5 days, or until 85-90% confluent, changing medium every 2 to 3 days. At 85-90% confluence, passage M1 cells were harvested by trypsinization and replated at $2 \times 10^6$ cells per T225 flask as described above, to generate passage M2 cultures. M2 cultures were fed fresh medium every three days, if necessary. When passage M2 cultures reached 85-90% confluence (usually within 3-5 days), they were either harvested for transfection to generate NRCs (Example 2 below) or frozen for future use.

Example 2: Preparation of Neural Regenerating Cells (NRCs)

Neural regenerating cells, also known as NRCs or SB623 cells, were prepared from MASCs harvested from passage M2 cultures, as follows.

A. Preparation of Transfection Mixture

Neural regenerating cells were made by transfection of passage M2 MASCs with a plasmid encoding the Notch intracellular domain. The plasmid (pN2) comprised a pCI-neo backbone (Promega, Madison, Wis.) in which sequences encoding amino acids 1703-2504 of the human Notch-1 protein, which encode the intracellular domain, were introduced into the multiple cloning site. For each flask of MASCs, 5 ml of transfection mixture, containing 40 μg of plasmid and 0.2 ml of Fugene 6® solution, was used. To make the transfection mixture, the appropriate amount of Fugene® solution (depending on the number of flasks of cells to be transfected) was added to αMEM in a sterile 250 ml tube, using a glass pipette. The solution was mixed gently and incubated for 5 min at room temperature. The appropriate amount of plasmid DNA was then added dropwise to the Fugene/αMEM mixture, gently mixed, and incubated for 30 min at room temperature.

Prior to the addition of pN2 DNA to the Fugene®/MEM mixture, 5 ml was removed and placed into a 15 ml tube to which was added 40 ug of pEGFP plasmid. This solution was used to transfect one flask of cells, as a control for transfection efficiency.

B. Transfection

For transfection, passage M2 MASCs were harvested by trypsinization (as described in Example 1) and plated at a density of $2.5 \times 10^6$ cells in 40 ml of growth medium per T225 flask. When the cells reached 50-70% confluence (usually within 18-24 hours) they were prepared for transfection, by replacing their growth medium with 35 ml per flask of transfection medium (αMEM+10% FBS without penicillin/streptomycin).

Three hours after introduction of transfection medium, 5 ml of the transfection mixture (Section A above) was added to each T-225 flask by pipetting directly into the medium, without contacting the growth surface, followed by gentle mixing. A control T-225 flask was transfected with 40 μg of pEGFP plasmid, for determination of transfection efficiency.

After incubating cultures at 37° C. in transfection medium for 24 hours, the transfection medium was replaced with αMEM+10% FBS+penicillin/streptomycin.

C. Selection of Transfected Cells

Cells that had incorporated plasmid DNA were selected 48 hrs after transfection by replacing the medium with 40 ml per flask of selection medium (growth medium containing 100 μg/ml G-418). Fresh selection medium was provided 3 days, and again 5 days after selection was begun. After 7 days, selection medium was removed and the cells were fed with 40 ml of growth medium. The cultures were then grown for about 3 weeks (range 18 to 21 days), being re-fed with fresh growth medium every 2-3 days.

Approximately 3 weeks after selection was begun, when surviving cells began to form colonies, cells were harvested. Medium was removed from the flasks using an aspirating pipette and 20 ml of DPBS without $Ca^{2+}/Mg^{2+}$, at room temperature, was added to each flask. The culture surface was gently rinsed, the wash solution was removed by aspiration and the rinse step was repeated. Then 10 ml of prewarmed (37° C.) 0.25% Trypsin/EDTA was added to each flask, rinsed over the growth surface, and the flasks were incubated for 5-10 min. at room temperature. Cultures were monitored with a microscope to ensure complete detachment of cells. When detachment was complete, trypsin was inactivated by addition of 10 ml of growth medium per flask. The mixture was rinsed over the culture surface, mixed by pipetting 4-5 times with a 10 ml pipette, and the suspension was transferred into a sterile 50 ml conical centrifuge tube. Cells harvested from several flasks could be pooled in a single tube. If any clumps were present, they were allowed to settle and the suspension was removed to a fresh tube.

The cell suspensions were centrifuged at 800 rpm (200×g) for 8 min at room temperature. Supernatants were removed by aspiration. Cell pellets were loosened by tapping the tube, about 10 ml of DPBS without $Ca^{2+}/Mg^{2+}$ was added to each tube and cells were resuspended by gently pipetting 4-5 times with a 10 ml pipette to obtain a uniform suspension.

D. Expansion of Transfected Cells

Cell number was determined for the suspension of transformed, selected cells and the cells were plated in T-225 flasks at $2 \times 10^6$ cells per flask (providing approximately 30% seeding of viable cells). This culture is denoted M2P1 (passage #1). M2P1 cultures were fed with fresh medium every 2-3 days, and when cells reached 90-95% confluence (usually 4-7 days after passage), they were harvested and replated at $2 \times 10^6$ cells per flask to generate passage M2P2. When M2P2 cultures reached 90-95% confluence, they were harvested for further assay.

Example 3: Comparison of Methylation Patterns Between MASCs and NRCs

MASCS were prepared from each of three independent human donors (denoted D33, D39 and D41), as described in Example 1 above. A portion of each preparation of MASCs was used to prepare neural regenerating cells, as described in Example 2, above. Genomic DNA was isolated from each of these six preparations of cells, and for each of the three donors, the methylation state of DNA from neural regenerating cells was compared to that of DNA from their MASC progenitor cells.

Genes whose methylation state were analyzed were selected according to three criteria:

1. known DNA methylation markers for MASCs and mesenchymal cell lines;
2. genes identified as methylation markers for MASCs in a genome-wide screen using differential methylation hybridization; and
3. genes reported in the literature to have an effect on embryonic stem cell differentiation.

For analysis of methylation status, bisulfite sequencing was performed on selected portions (amplicons) of genes selected according to the criteria listed above. Certain genes showed no significant differences in methylation status between MASCs and NRCs. These genes are listed in Table 1. A number of genes contained amplicons that exhibited differences in methylation status between MASCs and NRCs. These are listed in Table 2. Among these were five genes whose methylation differences were sufficiently significant to be useful in distinguishing NRCs from MASCs. These were PITX2 (also known as Pituitary homeobox 2; RIEG bicoid-related homeobox transcription factor), ROPN1L (Ropporin 1-like protein; AKAP-associated sperm protein), DNMT3b (DNA C5-N-Methyl Transferase 3b), IGF2R (Insulin-like growth factor 2 receptor) and SDF4 (Stromal cell-derived factor 4). Details of the methylation differences for selected amplicons in these five genes are provided in Tables 3-7.

Tables 3-7 show methylation state at a number of CpG sequences within each amplicon. "Control Cells" refer to MASCs, and "Target Cells" refer to NRCs. Cells were obtained from three different donors, and both MASCs and NRCs were prepared from each donor. SB101 MASCs and SB102 NRCs were from the same donor; SB 103 MASCs and SB 104 NRCs were obtained from a second donor, and SB105 MASCs and SB106 NRCs were obtained from a third donor. Each table show results obtained for a different amplicon. Columns 2-7 in each table show methylation levels for particular CpG sites within the amplicon (identified by the number following the colon in Column 1) in MASCs (columns 2-4) and NRCs (columns 5-7). Mean methylation level for each CpG assayed is provided in column 8 for MASCs and in column 9 for NRCs, and the difference in mean methylation level between MASCs and NRCs is shown in column 10.

Column 11 shows the "Fisher Score" for each CpG sequence assayed.

The Fisher Score is calculated as follows:

$$\frac{[\text{Mean methylation value } (MASCs) - \text{Mean methylation value } (NRCs)]^2}{[\text{Standard deviation } (MASCs)]^2 + [\text{Standard deviation } (NRCs)]^2}$$

The Fisher criterion indicates the variability in methylation levels at a particular CpG site. Fisher scores above 1 are considered significant.

These data show that methylation of CpG sequences in the PITX2, DNMT3b, IGF2R and SDF4 genes is increased in NRCs, compared to MASCs. In contrast, methylation of CpG sequences in the RPON1L gene is reduced in NRCs, compared to MASCs. Similarly, methylation of TMEM179 is decreased. In particular, demethylation of a methylated C residue at position 292 in amplicon 549 represents a significant difference in NRCs, compared to their MASC progenitor cells.

Accordingly, these methylation changes are diagnostic for NRCs; moreover, achieving the same methylation changes by other means is also useful for preparing NRCs.

TABLE 1

Amplicons showing no methylation differences between MASCs and NRCs

| Amplicon No. | Gene |
|---|---|
| 32 | CD4 precursor |
| 38 | Collagen α3 (VI) |
| 105 | Collagen α1 (II) |
| 112 | Prolargin precursor |
| 121 | Osteopontin |
| 127 | BMP4 |
| 135 | Anexin 6 |
| 179 | HIF 1A |
| 208 | GLI3 |
| 308 | Keratin 8 |
| 475 | LRRK 1 |
| 488 | KCTD 5 |
| 509 | Frizzled 1 precursor |
| 510 | HAND 2 |
| 514 | ZNF 74 |
| 522 | PKNOX 2 |
| 528 | GENSCAN 00000032124 |
| 532 | Q9C015 |
| 537 | C15orf27 |
| 546 | GENSCAN 00000000442 |
| 563 | GENSCAN 00000003261 |
| 824 | LIF |
| 827 | OCT4 |
| 830 | DNMT3B |
| 831 | IGF2R |
| 832 | IGF2R |
| 835 | SLUG |
| 836 | SLUG |
| 837 | PTN |
| 838 | PTN |
| 839 | ID3 |
| 840 | ID3 |
| 841 | ID4 |
| 842 | ID4 |
| 843 | SDF4 |

TABLE 1-continued

Amplicons showing no methylation differences between MASCs and NRCs

| Amplicon No. | Gene |
|---|---|
| 845 | KLF2 |
| 846 | KLF2 |
| 847 | P107/RBL1 |
| 848 | P107/RBL1 |
| 849 | RELN |
| 850 | RELN |
| 851 | SST |
| 852 | SST |

TABLE 2

Amplicons that are differentially methylated in MASCs and NRCs

| Amplicon ID | Gene |
|---|---|
| 18 | GDF5 |
| 164 | FGFR1 |
| 227 | LPIN1 |
| 825 | NANOG |
| 826 | NANOG |
| 834 | NNAT |
| 497 | PITX2 |
| 549 | ROPN1L |
| 829 | DNMT3b |
| 833 | IGF2R |
| 844 | SDF4 |
| 1303 | TMEM179 |

TABLE 3

Methylation changes in the PITX2 Gene

| CpG IDs | Control Cells | | | Target Cells | | | Mean Methylation | | Methylation Difference | Fisher Criterion |
| | SBI01 | SBI03 | SBI05 | SBI02 | SBI04 | SBI06 | Control | Target | | |
|---|---|---|---|---|---|---|---|---|---|---|
| AMP497: 62 | 1.00 | 1.00 | 1.00 | 0.97 | 0.97 | 1.00 | 1.00 | 0.98 | 0.02 | 1.33 |
| AMP497: 73 | 0.60 | 0.58 | 0.64 | 0.56 | 0.66 | 0.94 | 0.61 | 0.72 | −0.11 | 0.32 |
| AMP497: 82 | 0.80 | 0.79 | 0.80 | 0.67 | 0.82 | 0.98 | 0.80 | 0.82 | −0.03 | 0.03 |
| AMP497: 105 | 0.81 | 0.89 | 0.85 | 0.94 | 0.93 | 1.00 | 0.85 | 0.96 | −0.11 | 3.75 |
| AMP497: 109 | 0.64 | 0.69 | 0.77 | 0.66 | 0.87 | 0.96 | 0.70 | 0.83 | −0.13 | 0.60 |
| AMP497: 135 | 0.69 | 0.66 | 0.78 | 0.75 | 0.84 | 0.82 | 0.71 | 0.80 | −0.09 | 1.52 |
| AMP497: 139 | 0.76 | 0.77 | 0.83 | 0.96 | 0.89 | 1.00 | 0.79 | 0.95 | −0.16 | 5.88 |
| AMP497: 142 | 0.83 | 0.83 | 0.84 | 1.00 | 0.94 | 1.00 | 0.83 | 0.98 | −0.15 | 17.44 |
| AMP497: 153 | 0.76 | 0.76 | 0.88 | 0.92 | 1.00 | 0.97 | 0.80 | 0.96 | −0.16 | 4.15 |
| AMP497: 172 | 0.95 | 0.88 | 0.96 | 1.00 | 1.00 | 1.00 | 0.93 | 1.00 | −0.07 | 2.92 |
| AMP497: 184 | 0.84 | 0.77 | 0.92 | 1.00 | 1.00 | 1.00 | 0.84 | 1.00 | −0.16 | 4.77 |

TABLE 4

Methylation changes in the ROPN1L gene

| CpG IDs | Control Cells | | | Target Cells | | | Mean Methylation | | Methylation Difference | Fisher Criterion |
| | SBI01 | SBI03 | SBI05 | SBI02 | SBI04 | SBI06 | Control | Target | | |
|---|---|---|---|---|---|---|---|---|---|---|
| AMP549: 148 | 0.47 | 1.00 | 1.00 | 0.34 | 0.72 | 0.90 | 0.82 | 0.65 | 0.17 | 0.16 |
| AMP549: 167 | 0.39 | 0.83 | 0.83 | 0.02 | 0.28 | 0.80 | 0.68 | 0.37 | 0.32 | 0.45 |
| AMP549: 185 | 0.09 | 0.66 | 0.80 | 0.00 | 0.23 | 0.53 | 0.52 | 0.25 | 0.26 | 0.33 |
| AMP549: 190 | 0.12 | 0.66 | 0.66 | 0.00 | 0.43 | 0.47 | 0.48 | 0.30 | 0.18 | 0.20 |
| AMP549: 249 | 0.32 | 0.97 | 1.00 | 0.00 | 0.37 | 0.65 | 0.76 | 0.34 | 0.43 | 0.71 |
| AMP549: 292 | 1.00 | 1.00 | 1.00 | 0.38 | 0.55 | 1.00 | 1.00 | 0.64 | 0.36 | 1.25 |
| AMP549: 359 | 1.00 | 1.00 | NA | 1.00 | 1.00 | NA | 1.00 | 1.00 | 0.00 | NA |

TABLE 5

Methylation changes in the DNMT3b gene

| CpG IDs | Control Cells | | | Target Cells | | | Mean Methylation | | Methylation Difference | Fisher Criterion |
| | SBI01 | SBI03 | SBI05 | SBI02 | SBI04 | SBI06 | Control | Target | | |
|---|---|---|---|---|---|---|---|---|---|---|
| AMP829: 63 | 1.00 | 0.56 | 0.84 | NA | 1.00 | 0.92 | 0.80 | 0.96 | −0.16 | NA |
| AMP829: 67 | 0.56 | 0.52 | 0.63 | NA | 0.81 | 0.61 | 0.57 | 0.71 | −0.14 | NA |
| AMP829: 111 | 0.79 | 0.50 | 0.76 | 0.50 | 1.00 | 0.78 | 0.68 | 0.76 | −0.08 | 0.07 |
| AMP829: 116 | 0.80 | 0.58 | 0.75 | 0.39 | 1.00 | 0.72 | 0.71 | 0.70 | 0.01 | 0.00 |
| AMP829: 127 | 0.73 | 0.71 | 0.76 | 0.62 | 1.00 | 0.70 | 0.73 | 0.77 | −0.04 | 0.04 |
| AMP829: 134 | 1.00 | 1.00 | 0.76 | 0.93 | 0.84 | 1.00 | 0.92 | 0.92 | 0.00 | 0.00 |
| AMP829: 137 | 0.51 | 0.21 | 0.73 | 0.73 | 0.73 | 0.56 | 0.48 | 0.67 | −0.19 | 0.46 |
| AMP829: 140 | 1.00 | 0.58 | 0.45 | 0.60 | 0.38 | 0.74 | 0.68 | 0.57 | 0.10 | 0.09 |
| AMP829: 154 | 0.46 | 0.21 | 0.21 | 0.36 | 0.23 | 0.30 | 0.29 | 0.30 | 0.00 | 0.00 |

TABLE 5-continued

Methylation changes in the DNMT3b gene

| | Control Cells | | | Target Cells | | | Mean Methylation | | Methylation | Fisher |
|---|---|---|---|---|---|---|---|---|---|---|
| CpG IDs | SBI01 | SBI03 | SBI05 | SBI02 | SBI04 | SBI06 | Control | Target | Difference | Criterion |
| AMP829: 158 | 0.67 | 0.54 | 0.65 | 0.56 | 0.91 | 0.74 | 0.62 | 0.74 | −0.12 | 0.38 |
| AMP829: 186 | 0.21 | 0.16 | 0.14 | 0.20 | 0.26 | 0.26 | 0.17 | 0.24 | −0.07 | 1.96 |
| AMP829: 216 | 0.33 | 0.69 | 0.00 | 1.00 | 1.00 | 0.80 | 0.34 | 0.93 | −0.59 | 2.66 |
| AMP829: 298 | 0.08 | 0.06 | 0.00 | 0.53 | 0.12 | 0.00 | 0.05 | 0.22 | −0.17 | 0.37 |
| AMP829: 337 | 0.20 | 0.05 | 0.00 | 0.00 | 0.00 | 0.00 | 0.08 | 0.00 | 0.08 | 0.64 |
| AMP829: 358 | 0.03 | 0.01 | 0.00 | 0.17 | 0.00 | 0.00 | 0.01 | 0.06 | −0.04 | 0.19 |
| AMP829: 369 | 0.34 | 0.07 | 0.00 | 0.08 | 0.00 | 0.00 | 0.14 | 0.03 | 0.11 | 0.35 |

TABLE 6

Methylation changes in the IGF2R gene

| | Control Cells | | | Target Cells | | | Mean Methylation | | Methylation | Fisher |
|---|---|---|---|---|---|---|---|---|---|---|
| CpG IDs | SBI01 | SBI03 | SBI05 | SBI02 | SBI04 | SBI06 | Control | Target | Difference | Criterion |
| AMP833: 33 | 1.00 | 1.00 | 1.00 | 1.00 | 1.00 | 1.00 | 1.00 | 1.00 | 0.00 | NA |
| AMP833: 44 | 1.00 | 1.00 | 1.00 | 1.00 | 1.00 | 1.00 | 1.00 | 1.00 | 0.00 | NA |
| AMP833: 58 | 1.00 | 1.00 | 1.00 | 1.00 | 1.00 | 1.00 | 1.00 | 1.00 | 0.00 | NA |
| AMP833: 82 | 1.00 | 1.00 | 0.83 | 1.00 | NA | 1.00 | 0.94 | 1.00 | −0.06 | NA |
| AMP833: 102 | 1.00 | 0.91 | 1.00 | 1.00 | 1.00 | 1.00 | 0.97 | 1.00 | −0.03 | 0.33 |
| AMP833: 104 | 1.00 | 1.00 | 1.00 | 1.00 | 1.00 | 1.00 | 1.00 | 1.00 | 0.00 | NA |
| AMP833: 116 | 1.00 | 0.94 | 0.84 | 1.00 | 1.00 | 1.00 | 0.93 | 1.00 | −0.07 | 0.82 |
| AMP833: 118 | 1.00 | 1.00 | 1.00 | 1.00 | 1.00 | 1.00 | 1.00 | 1.00 | 0.00 | NA |
| AMP833: 146 | 1.00 | 1.00 | 1.00 | 1.00 | 1.00 | 1.00 | 1.00 | 1.00 | 0.00 | NA |
| AMP833: 155 | 1.00 | 1.00 | 1.00 | 1.00 | 1.00 | 1.00 | 1.00 | 1.00 | 0.00 | NA |
| AMP833: 162 | 1.00 | 1.00 | 1.00 | 1.00 | 1.00 | 1.00 | 1.00 | 1.00 | 0.00 | NA |
| AMP833: 164 | 1.00 | 1.00 | 1.00 | 1.00 | 1.00 | 1.00 | 1.00 | 1.00 | 0.00 | NA |
| AMP833: 176 | 0.82 | 0.83 | 0.87 | 1.00 | 1.00 | 1.00 | 0.84 | 1.00 | −0.16 | 36.57 |
| AMP833: 178 | 0.72 | 0.77 | 0.92 | 1.00 | 1.00 | 1.00 | 0.80 | 1.00 | −0.20 | 3.57 |
| AMP833: 191 | 0.77 | 0.85 | 0.85 | 0.97 | 1.00 | 0.96 | 0.82 | 0.98 | −0.15 | 9.16 |
| AMP833: 193 | 0.87 | 0.92 | 0.88 | 0.97 | 1.00 | 1.00 | 0.89 | 0.99 | −0.10 | 10.00 |
| AMP833: 217 | 0.76 | 0.74 | 0.77 | 0.86 | 0.90 | 0.88 | 0.76 | 0.88 | −0.12 | 24.02 |
| AMP833: 230 | 0.74 | 0.83 | 0.82 | 0.94 | 0.90 | 0.93 | 0.80 | 0.92 | −0.13 | 5.60 |
| AMP833: 239 | 0.59 | 0.80 | 0.81 | 0.92 | 0.84 | 0.89 | 0.73 | 0.88 | −0.15 | 1.32 |
| AMP833: 246 | 0.64 | 0.79 | 0.78 | 0.89 | 0.87 | 0.87 | 0.74 | 0.88 | −0.14 | 2.73 |
| AMP833: 248 | 0.66 | 0.80 | 0.76 | 0.83 | 0.85 | 0.84 | 0.74 | 0.84 | −0.10 | 1.80 |
| AMP833: 265 | 0.65 | 0.76 | 0.75 | 0.87 | 0.86 | 0.85 | 0.72 | 0.86 | −0.14 | 5.09 |
| AMP833: 277 | 0.65 | 0.73 | 0.73 | 0.87 | 0.84 | 0.84 | 0.70 | 0.85 | −0.15 | 8.98 |
| AMP833: 291 | 0.52 | 0.75 | 0.49 | 0.71 | 0.74 | 0.70 | 0.59 | 0.72 | −0.13 | 0.82 |
| AMP833: 306 | 0.48 | 0.66 | 0.60 | 0.76 | 0.69 | 0.67 | 0.58 | 0.71 | −0.13 | 1.51 |
| AMP833: 321 | 0.46 | 0.56 | 0.50 | 0.70 | 0.67 | 0.67 | 0.51 | 0.68 | −0.17 | 10.60 |
| AMP833: 347 | 0.47 | 0.64 | 0.53 | 0.48 | 0.70 | 0.63 | 0.55 | 0.60 | −0.06 | 0.15 |
| AMP833: 356 | 0.45 | 0.53 | 0.34 | 0.61 | 0.51 | 0.59 | 0.44 | 0.57 | −0.13 | 1.41 |
| AMP833: 360 | 0.41 | 0.47 | 0.41 | 0.61 | 0.51 | 0.51 | 0.43 | 0.54 | −0.11 | 2.96 |
| AMP833: 383 | 0.40 | 0.48 | 0.40 | 0.64 | 0.60 | 0.57 | 0.43 | 0.60 | −0.18 | 9.60 |
| AMP833: 385 | 0.34 | 0.51 | 0.44 | 0.53 | 0.62 | 0.56 | 0.43 | 0.57 | −0.14 | 2.09 |
| AMP833: 399 | 0.53 | 0.49 | 0.35 | 0.62 | 0.66 | 0.52 | 0.46 | 0.60 | −0.14 | 1.43 |
| AMP833: 401 | NA | 0.42 | 0.32 | 0.49 | 0.61 | 0.47 | 0.37 | 0.52 | −0.15 | NA |
| AMP833: 416 | NA | 0.42 | 0.33 | 0.60 | 0.76 | 0.32 | 0.38 | 0.56 | −0.19 | NA |
| AMP833: 418 | NA | 0.29 | 0.33 | 0.48 | 0.45 | 0.21 | 0.31 | 0.38 | −0.07 | NA |

TABLE 7

Methylation changes in the SDF4 gene

| | Control Cells | | | Target Cells | | | Mean Methylation | | Methylation | Fisher |
|---|---|---|---|---|---|---|---|---|---|---|
| CpG IDs | SBI01 | SBI03 | SBI05 | SBI02 | SBI04 | SBI06 | Control | Target | Difference | Criterion |
| AMP844: 215 | 0.29 | 0.00 | 0.59 | 0.48 | NA | 0.68 | 0.29 | 0.58 | −0.29 | NA |
| AMP844: 221 | 0.52 | 0.00 | 0.80 | 0.72 | NA | 1.00 | 0.44 | 0.86 | −0.42 | NA |
| AMP844: 224 | 0.40 | 0.00 | 0.51 | 0.89 | NA | 0.66 | 0.30 | 0.77 | −0.47 | NA |
| AMP844: 235 | 0.67 | 0.00 | 0.77 | 0.49 | 0.59 | 1.00 | 0.48 | 0.69 | −0.21 | 0.18 |
| AMP844: 237 | 0.43 | 0.00 | 0.79 | 0.91 | 0.66 | 0.93 | 0.41 | 0.83 | −0.43 | 1.03 |
| AMP844: 240 | 0.74 | 0.00 | 0.71 | 1.00 | 0.55 | 0.97 | 0.48 | 0.84 | −0.36 | 0.53 |

TABLE 7-continued

Methylation changes in the SDF4 gene

| | Control Cells | | | Target Cells | | | Mean Methylation | | Methylation | Fisher |
|---|---|---|---|---|---|---|---|---|---|---|
| CpG IDs | SBI01 | SBI03 | SBI05 | SBI02 | SBI04 | SBI06 | Control | Target | Difference | Criterion |
| AMP844: 243 | 0.47 | 0.00 | 0.87 | 0.58 | 0.15 | 0.89 | 0.45 | 0.54 | −0.09 | 0.03 |
| AMP844: 272 | 0.32 | 0.13 | 0.72 | 0.64 | 0.38 | 0.79 | 0.39 | 0.60 | −0.22 | 0.35 |
| AMP844: 275 | 0.40 | 0.07 | 0.60 | 0.60 | 0.06 | 0.45 | 0.36 | 0.37 | −0.01 | 0.00 |
| AMP844: 278 | 0.35 | 0.12 | 0.77 | 0.77 | 0.57 | 0.77 | 0.41 | 0.70 | −0.29 | 0.71 |
| AMP844: 303 | 0.43 | 0.30 | 0.56 | 1.00 | 0.31 | 0.82 | 0.43 | 0.71 | −0.28 | 0.54 |
| AMP844: 340 | 0.65 | 0.42 | 0.74 | 0.71 | 0.27 | 0.88 | 0.60 | 0.62 | −0.01 | 0.00 |
| AMP844: 342 | 1.00 | 0.77 | 1.00 | 0.72 | 0.29 | 1.00 | 0.92 | 0.67 | 0.25 | 0.44 |
| AMP844: 375 | 0.48 | 0.10 | 0.41 | 0.43 | 0.65 | 0.61 | 0.33 | 0.56 | −0.23 | 1.01 |
| AMP844: 393 | 0.32 | 0.07 | 0.65 | 0.21 | 0.49 | 0.51 | 0.35 | 0.40 | −0.06 | 0.03 |
| AMP844: 417 | 0.43 | 0.23 | NA | 0.64 | 0.43 | 0.61 | 0.33 | 0.56 | −0.23 | NA |
| AMP844: 426 | 0.26 | 0.12 | NA | 0.56 | 0.27 | 0.58 | 0.19 | 0.47 | −0.28 | NA |

Example 4: Changes in Methylation State of the ROPN1L Gene

The nucleotide sequences of the amplicons containing changes in methylation status in the ROPN1L gene in NRCs, compared to MASCs, were analyzed to identify precisely the nucleotides whose methylation state was altered. The results of this analysis are presented in Table 8.

TABLE 8

Methylation changes at specific cytosine residues in the ROPN1L gene

| Amplicon number | Sequence in: | |
|---|---|---|
| | MASCs | NRCs |
| 549:148 | T-T-A-$C^{me}$-G-C-C-T | T-T-A-C-G-C-C-T |
| 549:167 | T-C-T-$C^{me}$-G-G-A-G | T-C-T-C-G-G-A-G |
| 549:185 | C-C-T-$C^{me}$-G-G-G-G | C-C-T-C-G-G-G-G |
| 549:190 | G-G-A-$C^{me}$-G-A-T-C | G-G-A-C-G-A-T-C |
| 549:249 | C-C-T-$C^{me}$-G-G-C-C | C-C-T-C-G-G-C-C |
| 549:292 | C-A-T-$C^{me}$-G-C-C-C | C-A-T-C-G-C-C-C |
| 549:359 | G-T-C-$C^{me}$-G-A-T-G | G-T-C-C-G-A-T-G |

Example 5: Neural Regenerating Properties of NRCs with Altered DNA Methylation

Neural regenerating cells prepared as described in Example 2, which have the methylation changes described in Examples 3 and 4, are useful in the treatment of various disorders of the central and peripheral nervous systems. See, for example, co-owned WO 2009/023251 (Feb. 19, 2009); the disclosures of which is incorporated by reference in its entirety for all purposes.

The cells described and characterized in the present disclosure can also be converted, after further treatments, into cells that have the properties of neural cells and neural precursor cells. See, for example, US Patent Application Publication No. 2006/0166362 (Jul. 27, 2006), the disclosure of which is incorporated by reference, which discloses such exemplary treatments, and the properties of the cells so treated. See also US Patent Application Publication No. 2006/0216276 (Sep. 28, 2006), the disclosure of which is incorporated by reference, which discloses additional properties of cells so treated.

What is claimed is:

1. A method for converting a marrow adherent stromal cell (MASC) to a neural regenerating cell (NRC); the method comprising:
   altering the methylation state of one or more genes in the MASC, wherein the alterations comprise:
   (a) increased methylation of the PITX2, DNMT3b, IGF2R and SDF4 genes; and
   (b) decreased methylation of the ROPN1L and TMEM179 genes.

2. The method of claim 1, wherein the methylation state of the PITX2, DNMT3b, IGF2R and SDF4 genes is increased by contacting the MASC with one or more fusion proteins comprising a methylation domain and a DNA-binding domain, or with one or more nucleic acids encoding a fusion protein comprising a methylation domain and a DNA-binding domain, wherein the DNA-binding domains are engineered to bind to one or more sequences in each of the PITX2, DNMT3b, IGF2R and SDF4 genes.

3. The method of claim 1, wherein the methylation state of the ROPN1L and TMEM179 genes is decreased by contacting the MASC with one or more fusion proteins comprising a demethylation domain and a DNA-binding domain, or with one or more nucleic acids encoding a fusion protein comprising a demethylation domain and a DNA-binding domain, wherein the DNA-binding domains are engineered to bind to one or more sequences in each of the RPON1L and TMEM179 genes.

4. A neural regenerating cell that is descended from a MASC in vitro, wherein:
   (a) the cell supports the growth and/or regeneration of neural tissue;
   (b) the methylation state of one or more genes in the cell is altered compared to the MASC, wherein the alterations in methylation comprise:
      (i) increased methylation of the PITX2, DNMT3b, IGF2R and SDF4 genes, and
      (ii) decreased methylation of the ROPN1L and TMEM179 genes; and
   (c) during culture in vitro, neither the MASC nor any of its descendants were transfected with a polynucleotide comprising sequences encoding a Notch intracellular domain.

5. The neural regenerating cell of claim 4, wherein the methylation state of the PITX2, DNMT3b, IGF2R and SDF4 genes is increased by contacting the MASC with one or more fusion proteins comprising a methylation domain and a DNA-binding domain, or with one or more nucleic acids encoding a fusion protein comprising a methylation domain and a DNA-binding domain, wherein the DNA-binding domains are engineered to bind to one or more sequences in each of the PITX2, DNMT3b, IGF2R and SDF4 genes.

6. The neural regenerating cell of claim 4, wherein the methylation state of the ROPN1L and TMEM179 genes is decreased by contacting the MASC with one or more fusion proteins comprising a demethylation domain and a DNA-binding domain, or with one or more nucleic acids encoding a fusion protein comprising a demethylation domain and a DNA-binding domain, wherein the DNA-binding domains are engineered to bind to one or more sequences in each of the RPON1L and TMEM179 genes.

\* \* \* \* \*

SEQUENCE LISTING

<160> NUMBER OF SEQ ID NOS: 14

<210> SEQ ID NO 1
<211> LENGTH: 8
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (4)..(4)
<223> OTHER INFORMATION: Methylated nucleotide

<400> SEQUENCE: 1 catcgccc                                                          8

```
<210> SEQ ID NO 2
<211> LENGTH: 8
<212> TYPE: DNA
<213> ORGANISM: Artificial Sequence
<220> FEATURE:
<223> OTHER INFORMATION: Synthetic oligonucleotide

<400> SEQUENCE: 2 catcgccc                                                                  8

<210> SEQ ID NO 3
<211> LENGTH: 8
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (4)..(4)
<223> OTHER INFORMATION: Methylated nucleotide

<400> SEQUENCE: 3 ttacgcct                                                                  8

<210> SEQ ID NO 4
<211> LENGTH: 8
<212> TYPE: DNA
<213> ORGANISM: Artificial Sequence
<220> FEATURE:
<223> OTHER INFORMATION: Synthetic oligonucleotide

<400> SEQUENCE: 4 ttacgcct                                                                  8

<210> SEQ ID NO 5
<211> LENGTH: 8
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (4)..(4)
<223> OTHER INFORMATION: Methylated nucleotide

<400> SEQUENCE: 5 tctcggag                                                                  8

<210> SEQ ID NO 6
<211> LENGTH: 8
<212> TYPE: DNA
<213> ORGANISM: Artificial Sequence
<220> FEATURE:
<223> OTHER INFORMATION: Synthetic oligonucleotide

<400> SEQUENCE: 6 tctcggag                                                                  8

<210> SEQ ID NO 7
<211> LENGTH: 8
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (4)..(4)
<223> OTHER INFORMATION: Methylated nucleotide
```

-continued

<400> SEQUENCE: 7 cctcgggg                                                                          8

<210> SEQ ID NO 8
<211> LENGTH: 8
<212> TYPE: DNA
<213> ORGANISM: Artificial Sequence
<220> FEATURE:
<223> OTHER INFORMATION: Synthetic oligonucleotide

<400> SEQUENCE: 8 cctcgggg                                                                          8

<210> SEQ ID NO 9
<211> LENGTH: 8
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (4)..(4)
<223> OTHER INFORMATION: Methylated nucleotide

<400> SEQUENCE: 9 ggacgatc                                                                          8

<210> SEQ ID NO 10
<211> LENGTH: 8
<212> TYPE: DNA
<213> ORGANISM: Artificial Sequence
<220> FEATURE:
<223> OTHER INFORMATION: Synthetic oligonucleotide

<400> SEQUENCE: 10 ggacgatc                                                                          8

<210> SEQ ID NO 11
<211> LENGTH: 8
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (4)..(4)
<223> OTHER INFORMATION: Methylated nucleotide

<400> SEQUENCE: 11 cctcggcc                                                                          8

<210> SEQ ID NO 12
<211> LENGTH: 8
<212> TYPE: DNA
<213> ORGANISM: Artificial Sequence
<220> FEATURE:
<223> OTHER INFORMATION: Synthetic oligonucleotide

<400> SEQUENCE: 12 cctcggcc                                                                          8

<210> SEQ ID NO 13
<211> LENGTH: 8
<212> TYPE: DNA
<213> ORGANISM: Artificial Sequence
<220> FEATURE:
<223> OTHER INFORMATION: Synthetic oligonucleotide

```
<220> FEATURE:
<221> NAME/KEY: misc_feature
<222> LOCATION: (4)..(4)
<223> OTHER INFORMATION: Methylated nucleotide

<400> SEQUENCE: 13 gtccgatg                                                              8

<210> SEQ ID NO 14
<211> LENGTH: 8
<212> TYPE: DNA
<213> ORGANISM: Artificial Sequence
<220> FEATURE:
<223> OTHER INFORMATION: Synthetic oligonucleotide

<400> SEQUENCE: 14 gtccgatg                                                              8
```